US00PP27825P2

(12) United States Plant Patent
Zaiger et al.

(10) Patent No.: US PP27,825 P2
(45) Date of Patent: Apr. 4, 2017

(54) INTERSPECIFIC TREE NAMED 'AUTUMN CHARM'

(50) Latin Name: **Interspecific *Prunus* species**
Varietal Denomination: Autumn Charm

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 14/998,551

(22) Filed: Jan. 20, 2016

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of large size, yellow flesh fruit.
3. Fruit with very good flavor and eating quality.
4. Fruit with an attractive red skin color.
5. Fruit with good handling and storage quality.

1 Drawing Sheet

Botanical designation: Interspecific *Prunus* species.
Variety denomination: 'Autumn Charm'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of interspecific trees, which are known to us, and mentioned herein, 'Fall Fiesta' Interspecific (U.S. Plant Pat. No. 22,428), 'Autumn Bliss' Interspecific (U.S. Plant Pat. No. 24,665) and our proprietary non-patented interspecific selections '51ME458', '34M361', '38GH186' and '45GH93'.

STATEMENT REGARDING FEDERALLY SPONSORED RESEARCH AND DEVELOPMENT

Not applicable.

ORIGIN OF THE VARIETY

The new and distinct variety of interspecific tree consisting of multiple crosses between *Prunus salicina* and *Prunus armeniaca* was developed by us in our experimental orchard located near Modesto, Calif. from seed of our open pollinated proprietary non-patented interspecific seedling with the field identification number '51ME458'. The non-patented interspecific seed parent (51ME458) originated as a first generation cross of 'Autumn Bliss' Interspecific (U.S. Plant Pat. No. 24,665) and our non-patented proprietary interspecific seedling selection '34M361'. The interspecific seedling selection '34M361' originated as a second generation seedling from the cross of our proprietary non-patented interspecific seedlings '38GH186' and '45GH93'. A large number of these open pollinated seedlings were budded onto older established trees of 'Nemaguard' Rootstock (non-patented) to induce earlier maturity and fruit evaluation. Under close and careful observation the present seedling exhibited desirable tree and fruit characteristics and was selected in 2011 for additional asexual propagation and commercialization.

ASEXUAL REPRODUCTION OF THE VARIETY

In 2011 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree which consists of multiple crosses between plums and apricots is of large size, vigorous, upright growth and is a regular and productive bearer of large size, yellow flesh fruit with very good flavor and eating quality. The fruit is further characterized by having attractive red skin color and firm flesh that has good shipping and storage quality. In comparison to its immediate seed parent (51ME458) the fruit of the new variety is approximately 18 days earlier in maturity. In comparison to the commercial variety 'Fall Fiesta' Interspecific (U.S. Plant Pat. No. 22,428) the fruit of the new variety is larger in size and is approximately 18 days later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright growth, usually pruned to vase shape.

*Branching habit*.—Upright, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, adequate fruit set 3 consecutive years. No alternate bearing observed.

*Fertility*.—Self-sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 900 hours at or below 45° F.

Trunk:

*Size*.—Medium. Average circumference 44.5 cm at 27.9 cm above ground on a 5 year old tree.

*Stocky*.—Medium stocky.

*Texture*.—Medium shaggy, roughness increases with age of tree.

*Color*.—Varies from 10Y 5/2 to 7.5Y 5/2.

Branches:

*Size*.—Medium. Average circumference 14.0 cm at 1.2 meters above ground. Crotch angle approximately 30.0°, increases with heavy crop load.

*Surface texture*.—New growth relatively smooth. Mature growth medium rough, roughness increases with age.

*Lenticels*.—Average number 54 in a 25.8 square cm area. Average length 3.4 mm. Average width 1.4 mm. Color varies from 10YR 6/8 to 10YR 5/8.

*Color*.—New growth varies from 5GY 5/8 to 5YR 3/6. Mature growth varies from. 5YR 3/4 to 2.5YR 3/2, varies with age of growth.

Leaves:

*Size*.—Medium to large. Average length 107.7 mm. Average width 46.5 mm.

*Form*.—Ovate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 14.0 mm. Average width 1.7 mm. Longitudinally grooved. Surface — glabrous. Color varies from 5GY 5/8 to 5GY 5/6.

*Glands*.—Type — globose. Size — medium. Average length 1.1 mm. Average diameter 0.7 mm. Average number 3, varies from 2 to 5. Located primarily on the upper portion of the petiole and base of the leaf blade. Color varies from 5GY 8/8 to 2.5GY 7/8.

*Stipules*.—Average number 2. Average length 11.2 mm. Edges — pectinate. Color varies from 2.5GY 7/4 to 2.5GY 8/8.

*Color*.—Upper surface varies from 2.5GY 4/4 to 10Y 4/4. Lower surface varies from 10Y 5/4 to 10Y 6/4. Midvein color varies from 5GY 7/6 to 5GY 6/6.

Flower buds:

*Size*.—Medium to large. Average length 10.7 mm. Average diameter 5.4 mm.

*Hardiness*.—Hardy with respect to California winters.

*Density*.—Very dense.

*Form*.—Conical, becoming elongated just before opening.

*Pedicel*.—Average length 9.7 mm. Average width 0.9 mm. Surface — glabrous. Color varies from 5GY 8/8 to 5GY 8/10.

*Color*.—N 9.5/(white).

*Number of buds per spur*.—Average number 8, varies from 5 to 10. Varies with age of spur.

Flowers:

*Blooming period*.—Date of First Bloom Mar. 3, 2015. Date of Petal Fall Mar. 13, 2015, varies slightly with climatic conditions.

*Size*.—Medium. Average height 11.9 mm. Average diameter 20.8 mm.

*Petals*.—Number — normally 5, alternately arranged to sepals. Size — medium. Average length 10.3 mm. Average width 8.0 mm. Form— elliptical. Arrangement — free. Margin — sinuate. Both upper and lower surfaces glabrous. Color N 9.5/(white). Petal apex — rounded. Petal base — rounded to truncate.

*Sepals*.—Number — normally 5, alternately arranged to petals. Size — medium. Average length 3.8 mm. Average width 2.9 mm. Shape — triangular. Apex — triangular. Margin — entire. Color — upper surface 5GY 6/10. Lower surface 5GY 7/10. Both upper and lower surfaces glabrous.

*Stamens*.—Average number per flower 34, varies from 32 to 36. Average filament length 8.0 mm. On average, the stamens are above the height of the. petals. Filament color N 9.5/(white). Anther color varies from 2.5Y 7/10 to 5GY 8/10.

*Pollen*.—Present, self sterile, pollinator required. Color varies from 5Y 8/8 to 5Y 7/10.

*Pistil*.—Number — normally 1. Surface — glabrous. Average length 8.5 mm. Position of stigma an average of 1.9 mm below anthers. Color varies from 7.5Y 8.5/4 to 10Y 8.5/6.

*Fragrance*.—Heavy aroma.

*Color*.—N 9.5/(white).

*Pedicel*.—Average length 11.9 mm. Average width 0.9 mm. Surface — glabrous. Color varies from 2.5GY 6/10 to 5GY 7/10.

*Number flowers per flower bud*.—Average number 6, varies from 2 to 9.

Fruit:

*Maturity when described*.—Firm ripe, and ready for consumption.

*Date of first picking*.—Oct. 7, 2015.

*Date of last picking*.—Oct. 17, 2015, varies slightly with climatic conditions.

*Size*.—Large. Average diameter axially 73.3 mm. Average transversely in suture plane 66.8 mm. Average weight 198.8 grams, varies slightly with fertility of the soil, amount of thinning and climatic conditions.

*Form*.—Elongated.

*Suture*.—Slightly lipped.

*Ventral surface*.—Slightly lipped.

*Apex*.—Rounded to slightly pointed.

*Base*.—Flat.

*Stem cavity*.—Rounded to slightly elongated in suture plane. Average depth 6.4 mm. Average diameter 5.9 mm.

Stem:

*Size*.—Small to medium. Average length 9.1 mm. Average diameter 2.5 mm.

*Color*.—Varies from 2.5GY 5/8 to 10YR 3/4.

Flesh:

*Ripens*.—Evenly.

*Texture*.—Firm.

*Fibers*.—Few, small, tender.

*Firmness*.—Firm, comparable to other commercial interspecific varieties.

*Aroma*.—Slight.

*Amydgalin*.—Undetected.

*Eating quality*.—Very good.

*Flavor*.—Very good, with a good balance between acid and sugar.

*Juice*.—Moderate amount, enhances flavor.

*Acidity*.—Not available.

*Brix*.—Average Brix 16.0°, varies slightly with amount of fruit per tree and climatic conditions.

*Color*.—Varies from 10YR 8/6 to 10YR 7/8.

*Pit cavity*.—Average length 35.9 mm. Average width 20.5 mm. Average depth 7.3 mm. Color varies from 5YR 6/10 to 5YR 6/12.

Skin:

*Thickness*.—Medium.

*Surface*.—Slightly waffled.

*Bloom*.—Moderate amount, complete coverage.

*Tendency to crack*.—None.

*Color*.—Ground color varies from 7.5YR 7/10 to 5YR 7/10. Overspread with 7.5R 4/12 to 10R 3/8.

*Tenacity*.—Tenacious to the flesh.

*Astringency*.—Undetected.

Stone:

*Type*.—Freestone, weak adherence to flesh.

*Size*.—Medium to large. Average length 33.9 mm. Average width 18.5 mm. Average thickness 10.5 mm.

*Form*.—Ovoid.

*Base*.—Flat.

*Apex*.—Pointed. Average length 3.8 mm.

*Surface*.—Slightly pitted throughout, pits vary from rounded to elongated.

*Sides*.—Unequal, one side extending further from the suture plane.

*Ridges*.—A small ridge on each side of suture extending from base to apex.

*Tendency to split*.—None.

*Color*.—Varies from 7.5YR 6/6 to 5YR 5/8 when dry.

Kernel:

*Size*.—Small to medium. Average length 15.7 mm. Average width 8.1 mm. Average depth 4.8 mm.

*Form*.—Ovoid.

*Viability*.—Viable, complete embryo development.

*Skin color*.—Varies from 7.5YR 4/6 to 10YR 4/4.

Use: Dessert.

*Market*.—Local and long distance.

Keeping quality: Good, held firm in cold storage for 3 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

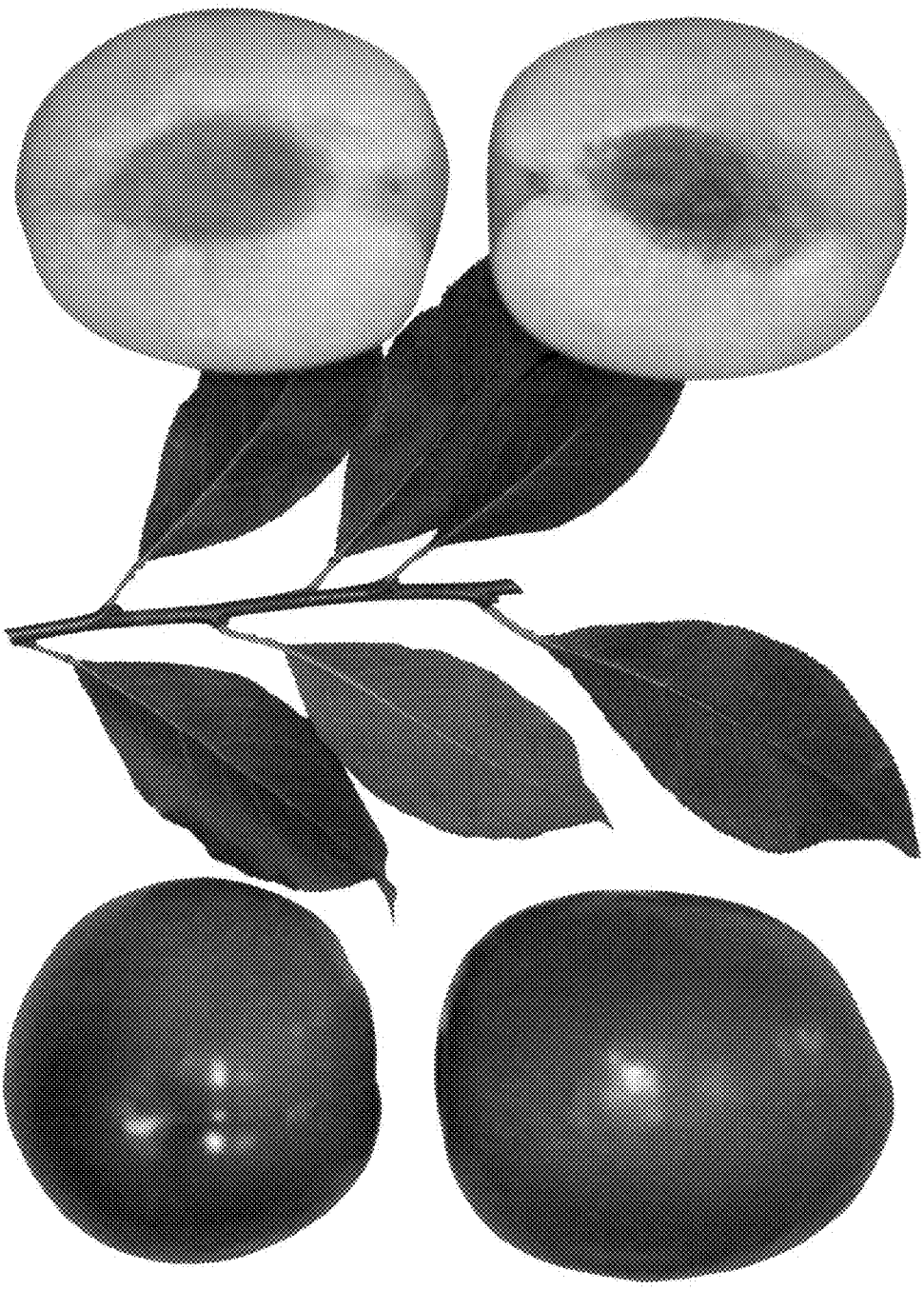

* * * * *